July 29, 1975
J. C. MIKKELSEN
Plant Pat. 3,751
BEGONIA PLANT
Filed May 31, 1974
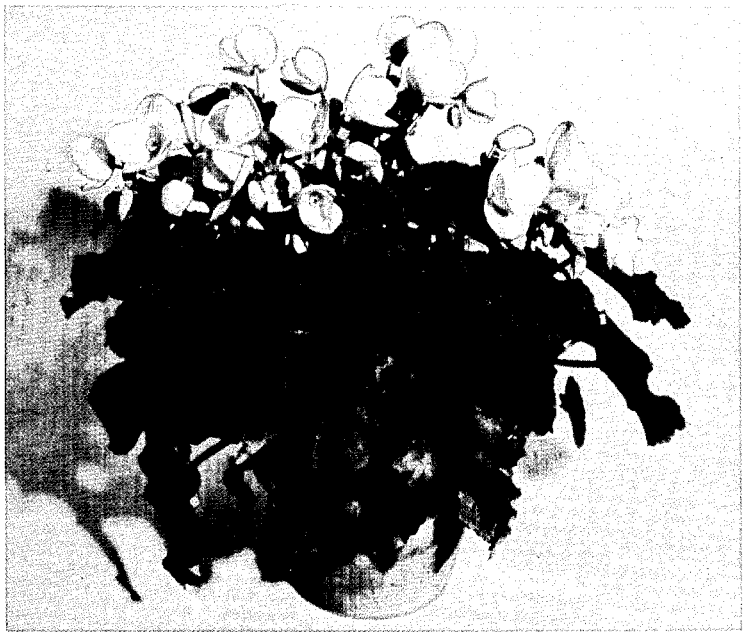

United States Patent

Plant Pat. 3,751

Patented July 29, 1975

3,751

BEGONIA PLANT

James C. Mikkelsen, Ashtabula, Ohio, assignor to Mikkelsens Inc., Ashtabula, Ohio

Filed May 31, 1974, Ser. No. 475,199

Int. Cl. A01h *5/00*

U.S. Cl. Plt.—68 1 Claim

ABSTRACT OF THE DISCLOSURE

The present invention relates to a new and distinctive variety of begonia plant, known by the varietal name Schwabenland Rose and botanically known as *Begonia elatior* (B × *hiemalis*-Fotsch.) The new cultivar was discovered as a mutation in a crop of the parent variety Improved Schwabenland Pink, disclosed in application Ser. No. 392,359, filed Aug. 28, 1973, in the name of James C. Mikkelsen, and assigned to Mikkelsens Inc., Ashtabula, Ohio. Improved Schwabenland Pink, in turn is a mutation of the unpatented cultivar Riegers Schwabenland Pink.

The new cultivar was discovered in a cultivated crop of the parent cultivar, and asexual reproduction by leaf and stem cuttings of the new mutation has reproduced the unique features of the new variety through successive propagations.

The following characteristics distinguish the new begonia from both its parent and other begonias commercially known and used in the floriculture industry:

1. The most distinguishing feature of the new cultivar is the bright rose colored flowers, with the color being an entirely newshade in the Rieger Schwabenland varieties.
2. The quantity of shoot initiation has been greatly improved; leaf cuttings consistently produce five to seven shoots at base of leaf petiole.
3. Rooting of leaf cuttings is faster than parent variety by several days; rooting at 22° C. is well established in 21 to 25 days.
4. Compared to parent the new cultivar is more floriferous and the flowers are clustered in the truss.
5. Flowers initiate and develop at several nodes at one time thereby presenting greater floral display.
6. Flowers are smaller than parent, measuring 4–6 cm. in diameter.
7. Overall growth is shorter compared to the parent. Average height for normal crops during fall and spring is 22 to 28 cm.
8. Leaf diameter is smaller and internodes closer, which allow new cultivar to produce smaller leaf cuttings for more efficient propagation.
9. Flower buds are not typically flat initially but oblong and rolled.

The accompanying colored photograph illustrates the overall appearance of this variety taken as a face view of the plant and showing the colors as true as it is reasonably possible to obtain in a colored reproduction of this type.

The following is a detailed description of the new begonia variety based on plants produced under commercial practices in Ashtabula, Ohio. It will be understood that growth rate, flower color, etc. may vary significantly with varying environmental conditions such as temperature, daylength and light intensity.

Color references are made to the Royal Horticultural Society Colour Chart except where general color terms of ordinary dictionary significance are used.

Parentage: A mutation of Improved Schwabenland Pink. The mutation occurred as a complete event in a single basal shoot.

Propagation: Successive and continuous propagation by leaf cuttings for nine months has confirmed that the mutation is stable in every aspect as shown by the flowering of plants from the propagations.

Rooting habit: Rapid; roots are fine, fibrous, and abundant.

Form: Plant form is upright, vigorous.

Habit of growth: Rapid from vegetative plants produced by propagating leaf cuttings; uniform development of shoots.

Blooming habits: Once flowering has initiated, the new cultivar continues to produce flowers rather indefinitely for six to eight months.

Blooming season: Normal flowering would occur in mid-November in Ohio. Controlled environment permits flowering 12 months of the year, with the poorest flower coloration occurring late June-early September.

Foliage: Above average quantity for Rieger begonias, alternate, at sharp angle to the main stem.

*Size.*—Overall smaller than most of the Rieger begonias, measuring 6–8 cm. wide by 8–10 cm. long.

*Texture.*—Firm, glabrous.

*Margin.*—Near perfect with less defined indentations.

*Color.*—Top, Green 137A. Under, Green 146A–B.

Disease resistance: Quite resistant to common powdery mildew when compared to older, more susceptible cultivars.

Flowers:

*Borne.*—In trusses, well dispersed throughout the plant, very floriferous.

*Quantity.*—Above average; more flowering initiating in more nodes, closer clustered flowering in the truss.

*Buds.*—Not typically flat but slightly rolled. Reverse color of tepals Red 50–A fading to 48–A.

*Tepals.*—Approaching 43C–D in tint but brighter in hue.

*Reproductive organs:* Stamens—loose but still distinctive. Anthers 17A–B. Pollen—Light yellow. Styles/ovaries—None observed to date.

I claim:

1. A new and distinct variety of begonia plant characterized particularly by its bright rose colored flowers; improved shoot initiation, with leaf cuttings consistently producing five to seven shoots at base of leaf petiole; fast rooting habit, with leaf cuttings being well established in 21 to 25 days at 22° C.; more floriferous habit, with the flowers being clustered in the truss; the initiation and development of flowers at several nodes at one time thereby presenting greater floral display; relatively small flowers, measuring 4–6 cm. in diameter; relatively short growth habit; relatively small leaf diameter with closer internodes, and by its flower buds which are initially oblong and rolled.

No references cited.

ROBERT E. BAGWILL, Examiner